United States Patent [19]
Alkemade et al.

[11] Patent Number: 6,139,844
[45] Date of Patent: Oct. 31, 2000

[54] METHOD FOR TREATING OR ELIMINATING A PARASITIC DISEASE

[75] Inventors: Stanley J. Alkemade, Arva; Catherine E. Hildebrand, London; Nigel C. Phillips, Pointe Claire; Dragan R. Rogan, London, all of Canada

[73] Assignee: Bioniche, Inc., London, Canada

[21] Appl. No.: 09/054,048

[22] Filed: Apr. 2, 1998

Related U.S. Application Data

[60] Provisional application No. 60/040,908, Apr. 2, 1997.

[51] Int. Cl.[7] .......................... A61K 39/02; A61K 39/38; A61K 39/04; A61K 39/10; A61K 39/008
[52] U.S. Cl. ...................................... 424/234.1; 424/282.1; 424/279.1; 424/248.1; 424/184.1; 424/240.1; 424/269.1; 424/278; 424/829; 424/245.1; 514/885
[58] Field of Search ............................... 424/829, 234.1, 424/282.1, 279.1, 248.1, 184.1, 245.1, 240.1, 269.1, 278.1; 514/885

[56] References Cited

U.S. PATENT DOCUMENTS

| | | |
|---|---|---|
| 3,956,481 | 5/1976 | Jolles et al. . |
| 4,152,423 | 5/1979 | Adams et al. . |
| 4,182,751 | 1/1980 | Ayme . |
| 4,337,243 | 6/1982 | Ayme . |
| 4,716,038 | 12/1987 | Stanford et al. . |
| 4,726,947 | 2/1988 | Shimada et al. . |
| 4,744,984 | 5/1988 | Ragland . |
| 4,837,202 | 6/1989 | Edwards et al. . |
| 4,954,622 | 9/1990 | Cooper . |
| 5,028,591 | 7/1991 | Edwards et al. . |
| 5,051,408 | 9/1991 | Cooper . |
| 5,336,666 | 8/1994 | Neway et al. . |
| 5,632,995 | 5/1997 | Wade et al. . |
| 5,759,554 | 6/1998 | Alkemade et al. . |
| 5,776,673 | 7/1998 | Tabor et al. . |

FOREIGN PATENT DOCUMENTS

| | | |
|---|---|---|
| 0 158 075 | 10/1985 | European Pat. Off. . |
| 0 308 197 | 3/1989 | European Pat. Off. . |
| 0 343 480 | 11/1989 | European Pat. Off. . |
| 280695 | 7/1990 | German Dem. Rep. . |
| 87/02679 | 5/1987 | WIPO . |
| 94/16727 | 8/1994 | WIPO . |
| 97/33612 | 9/1997 | WIPO . |
| WO 98 43656 | 10/1998 | WIPO . |

OTHER PUBLICATIONS

Carlos R. Bautista, et al., Effect of Three Immunostimulants on the Resistance Against *Trichiness spiralis* Infection in Mice[1], vol. 26, No. 1 pp. 91–93, 1995.
Baustista–Garfias et al, Archives of Medical Res. 26/1:91–93, 1995.
Vanselow, Vet. Bulletin, 57/11:881–896, 1987.
Oldham, JNCI 70/5:789–795, 1983.
Teth et al. Avian Diseases 31:861–867, 1987.
Coates et al, Avian Diseases, 21/2:319–322, 1977.
Lillehoj et al, Avian Diseases, 37:731–740, 1993.
Donahoe et al, JNCI, 60/4:829–833, 1978.
Hadden. Immunology Today 14/6:275–280, 1993.
Drews, Klin. Wochenschr. 62:254–264, 1984.
Cormack et al Equine Practice 13/8:18–22, 1991.
Ten Hagen et al, J Immunology 151/12:7077–7085, 1993.
Korbelik et al, J. Photochem. & Photobiol B: Biology 44:151–158, 1998.
Robinson et al, Appl. Parasitiol, 37:23–31, 1996.
Kadchim et al, J. Urology, 149/4 Suppl. pp 270A Abstract 225, 1993.
Kumar et al, Acta Vet. Hungarica, 46(1):1–11, 1998.
Filion et al, British J. Cancer, 79(2):229–235, 1999.

*Primary Examiner*—Nita Minnifield
*Attorney, Agent, or Firm*—Jones & Askew, LLP

[57] ABSTRACT

A method for treating or eliminating a protozoal or parasitic disease in an animal in which a sufficient amount of a bacterial cell wall extract is administered to the animal having the protozoal or the parasitic disease. The cell wall extract is preferably a mycobacterial cell wall extract or a cornybacterium cell wall extract. The cell wall extract is most preferably a *Mycobacterium phlei* cell wall extract.

8 Claims, No Drawings

METHOD FOR TREATING OR ELIMINATING A PARASITIC DISEASE

CROSS REFERENCE TO RELATED APPLICATIONS

This application claims priority to U.S. Provisional application Ser. No. 60/040,908 filed Apr. 2, 1997.

FIELD OF THE INVENTION

The present invention relates to the field of microbiology and immunology and more particularly relates to the use of a bacterial cell wall extract as a therapeutic agent for preventing, treating or eliminating a protozoal disease in an animal.

BACKGROUND OF THE INVENTION

Protozoal and parasitic diseases in an animal are difficult to treat. Various medicaments have been used to treat various protozoal and parasitic diseases with limited success. The safety and effectiveness of these, medicaments depend, in large part, on the route of administration and on the type and severity of the protozoal or parasitic disease.

Babesiosis is one example of such a disease. In tropical regions, babesiosis is one of the most prevalent diseases that infects domestic animals including, but not limited to, horses, cattle and dogs. Babesia parasitize and multiply in erythrocytes. The natural defense mechanism used by the infected animal against this organism includes the destruction of infected erythrocytes by phagocytosis, particularly by macrophages, and cytotoxic lymphocytes.

The two most common species of Babesia infecting horses are *Babesia caballi* and *Babesia equi*. *B. equi* is the more pathogenic of these two species. Several vectors such as ticks, mosquitoes and certain varieties of sucker flies, transmit the *B. equi* organism from horse to horse. The clinical manifestations of babesiosis disease include fever, malaise, anorexia, anemia, jaundice and hemoglobinuria. In South American countries, it is estimated that 50% of all racing horses are infected with Babesia, which results in a decrease in racing performance.

Many medicaments have been used to treat babesiosis disease. Thus far, the best results have been achieved with the chemotherapeutic agent imidocarb 3,3'-di-2-imidazolin-2-ylcarbanilide). Imidocarb is highly effective in treating *B. caballi*, but only moderately effective for the treatment of *B. equi*. Unfortunately, the administration of midocarb causes several undesirable side effects such as excessive salivation, lacrimation, increased frequency of defecation, tachypnea and abdominal pain, leading to a colic of toxic origin. It is very important that the medicament used to treat babesiosis not only reduce the symptoms of the disease, but also eliminate the infection completely from the animal. This is necessary to prevent transmission of Babesia from an animal that, though symptomless, remains a carrier and can transmit the disease to a healthy animal.

Schistosomiasis is an example of a protozoal (platyhelminth) disease that infects animals and is a health problem of immense proportion. The disease is caused by infection with species of Schistosoma such as *S. mansoni, S. japonicum* and *S. haematobium*. This disease is characterized by symptoms including pulmonary inflammation, malaise, fever, anemia, diarrhea and abdominal pain. Most infected individuals undergo a debilitating course of chronic infections that can result in death.

Many medicaments have been used to treat schistosomiasis. Thus far, the best results have been achieved with the drug praziquantel (2-(cyclohexylcarbonyl)-1,2,3,6,7-11b-hexahydro-4H-pyrazino[2,1-a]isoquinolin-4-one]). However, as this drug does not prevent re-infection, it cannot prevent the further transmission and spread of the disease.

Trichinellosis is an example of a protozoal (nematode) disease. Trichinellosis, caused by members of the genus Trichinella, infects more than 100 species of vertebrates, including man, and has a worldwide distribution. Trichinella causes a severe inflammatory reaction in the intestine of the infected animal. This inflammatory reaction appears to result from a nonspecific immune response, which is T-cell dependent (Miller, HRP. 1984. *Veterinary Immunology and Immunopathology*, 6:167).

Numerous other examples of protozoal and parasitic diseases are known that have various sequelae and cause debilitating effects in infected individuals. Moreover, such diseases, because they are endemic in certain areas of the world, result in significant disruption of the social and economic development of these areas.

Therefore, what is needed is method for preventing, treating or eliminating a variety of protozoal and parasitic diseases, by administering to an animal, by a variety of administration routes, a therapeutic agent that is safe, effective, and causes minimal or no adverse side effects.

SUMMARY OF THE INVENTION

As used herein the term "disease" refers to an impairment of the normal state of a living animal or any of its components that interrupts or modifies the performance or the function of the animal or its components and is a response to specific infective agents such as protozoa and parasites.

A method for preventing, treating or eliminating a protozoal or parasitic disease in an animal is provided. In accordance with the method, a bacterial cell wall extract is administered to the animal in an amount sufficient to prevent, treat or eliminate the disease. The bacterial cell wall extract is safe, has minimal or no adverse side effects, and can be administered to animals such as, but not limited to, mammals, including humans; birds; fish; amphibians; and crustaceans that are infected with a protozoal or parasitic organism.

As the immune response is related to the whole body and is modulated and affected by many complex interactions, nonspecifc immune stimulation is capable of accelerating and amplifying many immune responses. Preparations of, but not limited to, yeast, bacterial, viral, plant, biotechnological and chemical origin are capable of non-specifically stimulating the immune system. Preparations from, but not limited to, Mycobacterium, Corynebacterium (Proprionebacterium), Nocardia, Rhodococcus, Bordetella, Listeria, and bacille Calmette-Guerin (BCG) have been used to non-specifically stimulate immune activity. Mycobacteria Rhodococci and Norcardia are the preferred bacteria. *Mycobacterium phlei* is the most preferred bacteria. The bacterial cell wall extract can be administered by routes known to those skilled in the art including, but not limited to, topical, oral, nasal, intravenous, subcutaneous and intramuscular administration.

When administered to an animal, the bacterial cell wall extract acts as a nonspecific immunostimulant. That is, as the immune response is related to the whole body and is modulated and affected by many complex interactions, non-specifc immune stimulation is capable of accelerating and amplifying many immune responses. Therefore, it is effective as a therapeutic agent in preventing, treating or eliminating disease caused by a variety of protozoal or parasitic organisms such as, but not limited to, Anaplasma, Babesia, Balantidium, Besnoitia, Chlamydia, Coccidia, Cryptospondium, Cytauxzoon, Eimeria Entamoeba, Eperythrozoon, Erlichia, Giardia, Haemobartonella, Hammondia, Isopora, Leishmania, Neorickettsia, Plasmodium, Pneumocystis, Rickettsia, Schistosoma, Sarcocystis, Theileria, Thrichinella, Toxoplasma, Trichomonas, Trypanosoma, Unicaria, Dipylidium, Echinococcuse, Taenia, Ancylostoma, Ascaris, Enterobius, Strongyloides, Strongylus, Toxocara, Toxascaris and Trichuris.

Briefly, the bacterial cell wall extract is prepared as follows. Bacteria are grown in liquid medium and harvested. The cell walls are prepared by disrupting the bacteria and then harvesting the disrupted bacteria by centrifugal sedimentation. The cell wall fraction (pellet from the centrifugation step) is deproteinized by digestion with proteolytic enzymes, treated with detergents, washed, and lyophilized. This fraction can be adsorbed to lipid droplets suspended in an appropriate adjuvant/stabilizer for administration to an infected animal or an animal exposed to protozoal disease. Administration of the bacterial cell wall extract described herein is particularly useful in treating blood-borne protozoal and parasitic diseases.

The administration of the bacterial cell wall extract described herein differs from conventional therapy in that it nonspecifically causes the immune system to be activated. This enhances the defense capabilities of the immune system, thereby ameliorating a variety of protozoal and parasitic diseases. Thus, the bacterial cell wall extract is effective in treating protozoal and parasitic diseases in an animal that does not have antibodies against the infecting organism.

Accordingly, it is an object of the present invention to provide a method that is effective in preventing or treating a protozoal or parasitic disease.

Another object of the present invention is to provide a method that is effective in preventing the recurrence of a protozoal or parastic disease.

Another object of the present invention is to provide a method that is effective in preventing reinfection with a protozoal or parasitic disease.

Another object of the present invention is to provide a method that is effective in eliminating a protozoal or parasitic disease.

Another object of the present invention to provide a method that is effective in reducing the spread of a protozoal or parasitic disease by eliminating the protozoal or parasitic disease from the animal.

Another object of the present invention is to provide a method that is effective in stimulating the immune system.

Another object of the present invention is to provide a method that does not cause adverse side effects in the recipient, including anaphylaxis.

Another object of the present invention is to provide a method that is non-toxic to the recipient.

Another object of the present invention is to provide a method that does not sensitize the recipient to tuberculin skin tests.

Another object of the present invention is to provide a method in which a variety of administration routes may be successfully employed.

These and other objects, features and advantages of the present invention will become apparent after a review of the following detailed description of the disclosed embodiment and the appended claims.

DETAILED DESCRIPTION OF THE INVENTION

A method for preventing, treating or eliminating a protozoal or parasitic disease in an animal is described herein. In accordance with the method, a bacterial cell wall extract is administered to an animal infected with a protozoal or parasitic infection in an amount sufficient to prevent, reduce or eliminate the infection. The bacterial cell wall extract can be administered to animals such as, but not limited to, humans and other mammals, birds, fish, amphibians, and crustaceans to treat or prevent protozoal or parasitic infection. The bacterial cell wall extract can be administered by routes known to those skilled in the art including, but not limited to, topical, oral, nasal, intravenous, subcutaneous and intramuscular administration.

The protozoal or parasitic infection treatment method is effective for preventing, treating or eliminating disease caused by a variety of protozoal and parasitic organisms such as, but not limited to, Anaplasma, Babesia, Balantidium, Besnoitia, Chlamydia, Coccidia, Cryptospondium, Cytauxzoon, Eimeria Entamoeba, Eperythrozoon, Erlichia, Giardia, Haemobartonella, Hammondia, Isopora, Leishmania, Neorickettsia, Plasmodium, Pneumocystis, Rickettsia, Schistosoma, Sarcocystis, Theileria, Thrichinella, Toxoplasma, Trichomonas, Trypanosoma, Unicaria, Dipylidium, Echinococcuse, Taenia, Ancylostoma, Ascaris, Enterobius, Strongyloides, Strongylus, Toxocara, Toxascaris and Trichuris. The method is particularly useful for treating blood-borne protozoal and parasitic diseases.

The method described herein differs from conventional therapy in that it nonspecifically stimulates or causes activation of the immune system of the animal infected with the protozoa or parasite. This immune system activation enhances the defense capabilities of the immune system, thereby ameliorating a variety of protozoal and parasitic diseases. Thus, the method is effective in treating protozoal and parasitic diseases in an animal that was not previously exposed and does not already possess antibodies to the infecting organism.

The treatment method of the present invention does not cause a positive tuberculin reaction in the recipient, rarely causes an anaphylactic response even upon repeated administration of the bacterial cell wall extract, and has minimal or no adverse side-effects. It is to be understood that administration of the bacterial cell wall extract is not an immunization process, but is a process for generally stimulating the immune system so the recipient's own immune system can eliminate the protozoal or parasitic disease. Thus, the protozoal and parasitic disease treatment method of the present invention is ideally suited for treatment of a protozoal and parasitic disease and provides a novel method in which conventional medicaments or immunizations are not utilized.

Bacterial Cell Wall Extract Preparation

Any bacterial species can be used to prepare the bacterial cell wall extract of the present invention including, but not limited to the genus, Mycobacterium, Corynebacterium Proprionebacterium, Nocardia, Rhodococcus, Bordetella, Listeria, and bacille Calmette-Guerin (BCG). Mycobacteria, Rhodococci and Norcardia are the preferred bacteria. *Mycobacterium phlei* is the most preferred bacteria. The preferred method for producing the bacterial cell wall extract is described in U.S. Pat. No. 4,744,984, which is incorporated herein by reference. Mycobacterial cell wall extract may be commercially obtained from Bioniche, Inc. (London, Ontario).

Briefly, the bacterial cell wall extract is prepared as follows. Bacteria are grown in liquid medium and harvested. The cell walls are prepared by disrupting the bacteria and then harvesting the disrupted bacteria by centrifugal sedimentation. The cell wall fraction, which is the pellet from the centrifugation step, is deproteinized by digestion with proteolytic enzymes, treated with detergents, washed, and lyophilized. This fraction can be adsorbed to lipid droplets suspended in an appropriate adjuvant or stabilizer prior to administration to an infected animal or an animal exposed to a protozoal or parasitic infection. Alternatively, the bacterial cell wall extract may be emulsified in an adjuvant prior to use. The adjuvant can be any one of many adjuvants known to those skilled in the art. The preferred adjuvant is an oil and water emulsion, which can be prepared by mixing the bacterial cell wall extract with oil, adding an aqueous buffer with detergent, and emulsifying the mixture by any one of several methods known to those skilled in the art. These methods include, but are not limited to, homogenization in a high-speed blender or Potter-Elvehjem homogenizer, sonication and microfluidization. In addition, the bacterial cell wall extract can be emulsified in a number of oils including, but not limited to, mineral oil (Drakeol 6-VR, Penreco, Butler, Pa.), squalane, squalene and the synthetic mineral oil n-hexadecane. It will be understood by those skilled in the art that the method of preparing the emulsion is not critical. Numerous variations of the composition of the oil and aqueous phases, their proportions and means of emulsification will be apparent to those skilled in the art and can be used with the bacterial cell wall extract in practicing the present method.

The preferred emulsions of bacterial cell wall extract are prepared by addition of between approximately 5 g and 15 g of dry, deproteinized bacterial cell wall to a dry, one-liter beaker. Mineral oil, squalene, squalane, or n-hexadecane is added at between approximately 10 ml and 50 ml per gram of cell walls. The suspension is covered and mixed for approximately 30 minutes to overnight. Approximately 10 ml aliquots of the cell wall/oil mixture are transferred to one liter beakers. Five hundred ml of sterile phosphate buffered saline (PBS) is added to each aliquot. Aliquots of approximately 6 ml to 7 ml of the mixture are homogenized by microfluidization using a Microfluidics Tabletop MICROFLUIDIZER™ model M-100Y at approximately 20,000 psi to 30,000 psi for one flow-through, transferred to sterile bottles, and stored at 4° C.

Optionally, aluminum hydroxide stabilizer may be added to the bacterial cell wall extract emulsion. Aluminum hydroxide is obtained as a 9.4% compressed gel from the Reheis Chemical Co. (Berkeley Heights, N.J.) and is hydrated to 1.3% aluminum oxide by the addition of deionized water. The gel is sterilized in an autoclave at 120° C. for 20 minutes before it is added to the bacterial cell wall extract emulsion. One liter of the final emulsion contains about 900 ml of emulsified bacterial cell wall extract, 50 ml of 1.3% aluminum oxide and 40 ml of added PBS. Thimerosal (ethylmercurithio-salicylate, Sigma Chemical Co., St. Louis, Mo.) and antibiotics including, but not limited to, gentamycin and amphoteracin B can be added as a preservative to the bacterial cell wall extract emulsion. The preferred concentration of thimerosal is about 0.1 g per liter, of gentamycin about 30 $\mu$g/ml and of amphoteracin B about 2.5 $\mu$g/ml.

Known active ingredients of the bacterial cell wall extract to be administered in the present method include the family of muramyl dipeptides and trehalose dimycolate, as well as any unknown active components which may be present in the deproteinized cell wall skeletons of bacteria. The present invention is effective in treating any parasitic or protozoal disorder in which the immune components of the body are present including, but not limited to, neutrophils, lymphocytes and macrophages. Although not wanting to be bound by the following hypothesis, it is thought that the method is effective in preventing, treating and eliminating a protozoal or a parasitic disease because the infecting organisms are in constant contact with the cells of the immune system of the body. Further, it is thought that the bacterial cell wall extract acts on these cells of the immune system to stimulate increased production of cytokines.

Bacterial Cell Wall Extract Formulation and Administration

The bacterial cell wall extract can be provided as a pharmaceutically acceptable composition using formulation methods known to those skilled in the art. Examples of formulation methods may be found in, for example, H. C. Ansel, et al., PHARMACEUTICAL DOSAGE FORMS AND DRUG DELIVERY SYSTEMS, 6th edition (Williams & Wilkins, Philadelphia 1995), incorporated herein by reference. Other formulations known to those skilled in the art also can be used. The formulations include, but are not limited to, those suitable for oral, rectal, urethral, ophthalmic, (including intravitreal or intracameral) nasal, topical (including buccal and sublingual), vaginal or parenteral (including subcutaneous, intramuscular, intravenous, intradermal, intratracheal, and epidural) administration.

The formulation may be conveniently presented in unit dosage forms prepared by conventional pharmaceutical techniques. Such techniques include the step of bringing into association the active ingredient and the pharmaceutical carriers or excipients. In general, the formulations are prepared by uniformly and intimately bringing into association the active ingredient with liquid carriers or finely divided solid carriers or both, and then, if necessary, shaping the product.

The method can be used with any one, all, or any combination of ingredients regardless of the carrier/vehicle used to present them to the responsive immune cells including, but not limited to, carriers such as liposomes, various non-degradable polymers and osmotic minipumps. In addition, the combinations may be incorporated into biodegradable polymers allowing for sustained release of the compound, the polymers being implanted in the vicinity of where drug delivery is desired. The biodegradable polymers and their use are described, for example, in Brem, et al. 1991. *Journal of. Neurosurgery*, 74:441–446, which is incorporated by reference herein.

Formulations of the present method suitable for oral administration may be presented as discrete units including, but not limited to, capsules, cachets or tablets, each containing a predetermined amount of the active ingredient; powders or granules; solutions or suspensions in an aqueous liquid or a non-aqueous liquid; oil-in-water liquid emulsion or water-in-oil emulsion and bolus.

A tablet may be made by compression or molding, optionally with one or more accessory ingredients. Compressed tablets may be prepared by compressing, in a suitable machine. The active ingredient, in a free-flowing form such as a powder or granule, optionally may be mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations of the present method suitable for topical administration in the mouth include lozenges comprising the ingredients in a flavored base, usually sucrose and acacia or tragacanth; pastilles comprising the active ingredient in an inert base such as gelatin and glycerin, or sucrose and acacia; and mouthwashes comprising the active ingredient to be administered in a suitable liquid carrier.

Formulations of the present method suitable for topical administration to the skin may be presented as emulsions, ointments, creams, gels, lotions and pastes comprising the active ingredient in such carriers as are known in the art to be appropriate.

Formulations of the present method for rectal administration may be presented as a suppository comprising the active ingredient with a suitable base, for example, cocoa butter or a salicylate.

Formulations of the present method suitable for nasal administration, wherein the carrier is a solid, include a coarse powder having a particle size, for example, in the range of 20 to 500 microns, which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations of the present method suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions that may contain anti-oxidants, buffers, bacteriostats and solutes which render the formulation isotonic with the blood of the intended recipient; and aqueous and non-aqueous sterile suspensions that may include suspending agents and thickening agents. The formulations for parenteral administration may be presented in unit-dose or multi-dose containers, for example, in sealed ampoules and vials, and may be stored in a freeze-dried (lyophilized) condition requiring only the addition of a sterile liquid carrier, for example, water for injection, immediately prior to use. Extemporaneous injection solutions and suspensions may be prepared from sterile powders, granules and tablets of the kind previously described.

The optimal dose of the bacterial cell wall extract to be administered varies with the size of the animal that is being treated and with the method of administration. Only an amount sufficient to stimulate the immune system is required. A single dose is from about 0.01 to 10 mg bacterial cell wall extract/ml, more preferably from about 0.05 to 6 mg bacterial cell wall extract/ml and most preferably from about 0.1 to 4.0 mg bacterial cell wall extract/ml. The bacterial cell wall extract is administered in a total volume of from about 0.01 to 10 ml, more preferably from about 0.05 to 7.5 ml and most preferably from about 0.1 to 5.0 ml.

The bacterial cell wall extract of the present method can be administered one time or multiple times to the same recipient. The dosage amounts and the dosage schedules can be determined readily by those skilled in the art. Preferred dosage formulations are those containing a dose or unit, a sub-dose or subunit, or other fraction thereof of bacterial cell wall extract in, but not limited to, the formulations disclosed herein. Further, it should be understood that in addition to the ingredients particularly mentioned herein, the present method may include other agents conventional in the art having regard to the type of formulation to be used.

The following examples will serve to further illustrate the present invention without, at the same time, however, constituting any limitation thereof.

EXAMPLE 1

PREPARATION OF *MYCOBACTERIUM PHLEI* CELL WALL EXTRACT

The preparation of *Mycobacterium phlei* cell wall extract as outlined in Example 1 is representative of the preparation of cell wall extracts from other bacterial species.

*M. phlei* was obtained from the Institut fur Experimental Biologie and Medizin, Borstel, West Germany, and was stored as a suspension in sterile milk at −60° C. Approximately eleven transfers of the isolate were made between 1976 and 1985 without any diminution of biological activity of the modified cell walls. The *M. phlei* was cultured on Petragnani medium (Difco Labs, Detroit, Mich.).

*M. phlei* cell walls were prepared with a Heat System sonicator (previously called a Branson sonicator) Model XL2015. Approximately 400 grams of moist cell mass was placed into a clean blender with a capacity of approximately 1200 ml. The cell mass was mixed at high speed for between 30 to 60 seconds. After mixing, 6 ml of Tween 80 and between 200 and 400 ml of sterile water were added to the cell mixture. The entire cell suspension was then mixed in the blender at low speed for about ten seconds.

Cell disruption was accomplished by ultrasonic cell disruption using a Heat System sonicator and a ¾ tapped horn. Five hundred milliliters of a cell suspension, wherein the cells comprise about 50% to 70% of the volume, were placed in a one liter beaker and sonicated at a setting of eight for about five minutes. The sonicate was stored in a sterile flask on ice during the fractionation process.

The sonicate was transferred to 250 ml centrifuge bottles and centrifuged for one hour at 27,500×g at 15° C. in an intermediate speed centrifuge with a GSA rotor. The supernatant fluid from the centrifugation was decanted and discarded. The undermost, white pellet of unbroken cells was discarded. The sedimented crude cell wall fraction was transferred to a blender and suspended in sterile, deionized water by mixing at low speed. The crude cell wall fraction was washed by resuspension and centrifugation at 27,500×g at 15° C. for one hour). Again, the undermost, white pellet of unbroken cells was discarded.

After washing the crude cell wall fraction, the pellet was resuspended in sterile, deionized water and spun for five minutes at 350×g to sediment unbroken cells while retaining the cell walls in the supernatant fluid. The supernatant fluid was decanted and centrifuged at 27,500×g for 1 hour at 15° C. to sediment the crude cell wall fraction.

The crude cell wall fraction was deproteinized by digestion with proteolytic enzymes. The crude cell wall fraction, derived from about 400 g of whole cells, was resuspended in 1 liter of 0.05 M Tris-HCl, pH 7.5, by mixing at low speed. After the crude cell wall fraction was thoroughly resuspended in the Tris buffer, 50 mg of trypsin (pancreatic trypsin, Sigma Chemical Co., St. Louis, Mo.) were added and the suspension was stirred using a magnetic stirring bar at 35° C. for six hours. Following trypsin treatment, 50 mg of pronase (*Streptomyces griseus* protease, Sigma Chemical Co., St. Louis, Mo.) were added to each liter of trypsin treated cell wall suspension. The suspension was stirred using a magnetic stirring bar for 12 to 18 hours at 35° C.

The protease digested cell wall fraction was treated with detergent and phenol. To each liter of cell wall suspension, 60 g of urea (J. T. Baker Chemical Co., Phillipsburg, N.J.), 2.0 ml of 100% Triton X-100 (polyoxyethylene ethers, Sigma Chemical Co., St. Louis, Mo.), and 100 g of phenol crystals (Fisher Scientific, Fair Lawn, N.J.) were added. The flask containing the suspension was covered loosely with aluminum foil, warmed to 60°–80° C. and stirred for one hour. The deproteinized cell wall fraction was spun for 10 minutes at 16,000×g in a GSA rotor. The supernatant fraction was decanted and discarded and the dark fluid beneath the pellet was removed using a disposable pipette. The cell wall pellet was washed 3 times by resuspension in about one liter of sterile water and centrifuged at 16,000×g for 10 minutes in a GSA rotor.

The washed, modified mycobacterial cell wall extract (MCWE) or cell wall pellet was lyophilized by transferring the suspension to a lyophilizing flask with a small amount of deionized sterile water. One 300 ml lyophilizing flask was used for each 30 grams of wet cell wall starting material. The cell wall suspension was shell frozen by rotating the flask in ethanol that had been cooled with solid carbon dioxide. After the content of the flask was frozen, the flask was attached to a lyophilization apparatus (Virtis Co., Inc., Gardiner, N.Y.) and lyophilized. After lyophilization, the sample was transferred to a sterile, screw-cap container and stored at –20° C. in a desiccator jar containing anhydrous calcium sulphate.

EXAMPLE 2

EMULSIFICATION OF BACTERIAL CELL WALL EXTRACT

Emulsions of a mycobacterial cell wall extract (MCWE) were prepared in four steps: (1) addition of dry, deproteinized, mycobacterial cell wall extract and squalane to an emulsification vessel, (2) suspension of the cell wall extract in the oil, (3) addition of buffered saline solution containing a detergent to the mixture of cell wall extract and oil, and (4) emulsification of the oil-cell wall extract complex into the aqueous detergent saline solution.

Emulsification was accomplished by microfluidization using a Microfluidics tabletop microfluidizer Model M-110Y at 10,700–23,000 psi for one flow-through. The typical volume run was six to seven liters per run. Several grams of lyophilized MCWE (prepared as described in Example 1, above) were added to a dry, sterile, one liter beaker. Squalane was added at a concentration of 20 ml per gram of MCWE and the mixture was covered and allowed to sit overnight. The optimum concentration of oil in the oil and water suspension is between approximately 1% and 7%. Ten ml aliquots of the oil-MCWE mixture were transferred to sterile one liter beakers. Five hundred milliliters of sterile, phosphate buffered saline (0.05M sodium phosphate, pH 7.2, 9 g NaCl and 2 ml Tween-80 per liter of deionized water) were added to each 10 ml aliquot of oil-MCWE. The mixture was homogenized by microfluidization and transferred to sterile, capped bottles for storage at 4° C. Samples of the emulsion were examined under a cover-slip with a light microscope to confirm that the oil droplets were small and granular in appearance rather than clear with dark borders. Granular appearing droplets indicate proper adsorption of the cell wall to the oil carrier.

Bottles of the cell wall preparation in oil-in-water emulsion were pooled in a sterile mixing vessel and, for intramuscular use, 50 ml of 1.3% aluminum oxide, 50 ml of phosphate buffered saline, 30 μg/ml gentamycin and 2.5 μg/ml amphoteracin B were added to each liter of cell wall emulsion as preservatives. Sterile Type I glass vials and plastic syringes were filled with from 1.5 ml to 10 ml of the stabilized emulsion under sterile laminar air flow using a Filamatic Vial Filler (National Instrument Co., Baltimore, Md.). The vials and syringes were capped, sealed and stored at 4° C.

EXAMPLE 3

TREATMENT OF *BABESIA EQUI* WITH MCWE

Treatment in Horses

Five mares, positive for *Babesia equi* in the complement fixation test, were used in this study. One of the mares was given four doses of 4 mg/kg imidocarb intramuscularly at 72 hour intervals. Four of the mares were given two doses of 1500 g of MCWE (prepared as described in Example 2, above) intramuscularly approximately fourteen days apart. The body temperature of each animal was monitored every six hours during the 24 hour period following the administration of the MCWE. Body temperature never increased more than 1.0° to 1.2° C. and was normal within 18 to 24 hours.

MARE 1—IMIDOCARB

Mare 1 had a *B. equi* antibody titre of ++++ at a 1/20 dilution prior to treatment with Imidocarb. Six months subsequent to treatment with Imidocarb, Mare 1 again tested positive for *B. equi.*

MARE 2—MCWE

Mare 2 had a *B. equi* antibody titre of + at a 1/5 dilution prior to treatment with MCWE. Six months subsequent to treatment with MCWE, Mare 2 tested negative for *B. equi.*

MARE 3—MCWE

Mare 3 had a *B. equi* antibody titre of ++++ at a 1/20 dilution prior to treatment with MCWE. Five months subsequent to treatment with MCWE, Mare 3 tested negative for *B. equi.*

MARE 4—MCWE

Mare 4 had a *B. equi* antibody titre of +++ at a 1/5 dilution prior to treatment with MCWE. Three months subsequent to treatment with MCWE, Mare 4 tested negative for *B. equi.*

MARE 5—MCWE

Mare 5 had a *B. equi* antibody titre of ++++ at a 1/40 dilution prior to treatment with MCWE. Three months subsequent to treatment with MCWE, Mare 5 tested negative for *B. equi.*

Treatment in Cattle

Twenty cows, positive for *B. equi,* were used in this study. The animals were treated with intramuscular MCWE (prepared as described in Example 2) at the Veterinary School of Medellin, Colombia. After MCWE treatment, the animals tested negative for *B. equi.*

These data show that MCWE is effective as a therapeutic agent for treating *B. equi* and for eliminating *B. equi* from an animal.

EXAMPLE 4

TREATMENT OF TRYPANOSOMIASIS WITH MCWE

Thirty horses infected with trypanosomes were used in this study. The horses were divided into three groups and were treated intramuscularly with diminazine MCWE (prepared as described in Example 2) or MCWE (prepared as described in Example 2) plus diminazine. MCWE alone and MCWE plus diminazine were equally effective in eliminating the trypanosomes from the horses. Diminazine alone was less effective than MCWE or MCWE plus diminazine in eliminating the trypanosomes from the horses.

These data show that MCWE is effective as a therapeutic agent for treating trypanosomiasis and in eliminating trypanosomes from an animal.

EXAMPLE 5

TREATMENT OF *EHRLICHIA RISTICII*, WITH MCWE

In this study, horses infected with *Ehrlichia risticii* were treated with a single dose of MCWE. Within four days of treatment, the animals had recovered from the *E. risticii* infection. With conventional medicaments, recovery time is usually from two to three weeks.

These data show that MCWE is effective as a therapeutic agent for treating the trypanosome *E. risticii*.

EXAMPLE 6

TREATMENT OF *SCHISTOSOMA MANSONI* WITH MCWE

Six week-old C57BL/5 mice (Charles River, Quebec) were used in this study. The mice were divided into 4 groups and were treated as shown in Table 1.

TABLE 1

TREATMENT GROUPS

| Group | 0 | 2 | 4 | 6 | 8 | 10 | 12 | 16 | 18 |
|---|---|---|---|---|---|---|---|---|---|
| I Post Exposure | | | | | | | | | |
| A   0 μg MCWE | | | C | O | | | TO | | |
| B  20 μg MCWE | | | C | M | | | TM | | |
| C 100 μg MCWE | | | C | M | | | TM | | |
| II Post Exposure | | | | | | | | | |
| A   0 μg MCWE | | | C/M | O | | | TO | | |
| B  20 μg MCWE | | | C/M | M | | | TM | | |
| C 100 μg MCWE | | | C/M | M | | | TM | | |
| III Pre Exposure | | | | | | | | | |
| A   0 μg MCWE | O | O | C | | | | T | | |
| B  20 μg MCWE | M | M | C | | | | T | | |
| C 100 μg MCWE | M | M | C | | | | T | | |
| IV Pre Exposure Post Exposure | | | | | | | | | |
| A   0 μg MCWE | O | O | C | | | O | O | O | T |
| B  20 μg MCWE | M | M | C | | | M | M | M | T |
| C 100 μg MCWE | M | M | C | | | M | M | M | T |

C=*S. mansoni* cercariae, collected from *Biomphalaria glabrata* snails (Lowell University, Lowell, Mass.), were concentrated and counted. Aliquots of 200 *S. mansoni* cercariae in 0.1 ml of saline were injected subcutaneously into the abdominal cavity of the mice. M=MCWE, emulsified in squalane and water (prepared as described in Example 2, above), at doses of 0 μg, 20 μg or 100 μg, were injected intraperitoneally into the mice. T=Termination. Mice were sacrificed by cervical dislocation, and worms recovered from each mouse and their number and gender determined.

Table 2 shows the effect of MCWE on worm burden in infected mice.

TABLE 2

EFFECT OF MCWE ON *S. mansoni* WORM BURDEN

| | Worm Recovery and Reduction[a] | | |
|---|---|---|---|
| Group MCWE | A 0 μg | B 20 μg | C 100 μg |
| Group I | 25.67 (± 4.71, 18) | 30.88   0% (± 3.70, 17) | 28.33   0% (± 3.20, 15) |
| Group II | 48.73 (± 5.08, 15) | 25.60  47.5%* (± 2.51, 15) | 42.47  13.3% (± 3.20, 15) |
| Group III | 24.53 (± 2.62, 15) | 17.29  29.5%* (± 1.56, 17) | 19.94  18.7%* (± 1.92, 16) |
| Group IV | 19.45 (± 3.60, 11) | 18.08   7% (± 2.34, 13) | 10.06  48.3%* (± 1.48, 17) |

*Significance as determined by Student t-test.

The standard error and the number of mice per group are indicated in the parentheses. [a]Worm-reduction was calculated as [control worms—experimental worms]/control worms×100%. *Significant as determined by Student's t-test.

In Group I (post exposure), the worm burden of control (A) mice, 20 μg MCWE (B) treated mice and 100 μg MCWE treated (C) mice were not significantly different. In Group 2 (post exposure), there was a significant reduction in worm burden in 20 μg MCWE treated (B) mice, but not in 100 μg MCWE treated (C) mice. In Group 3 (pre-exposure), there was a significant reduction in worm burden in both 20 μg MCWE treated (B) mice and in 100 μg MCWE treated (C) mice. In Group 4 (pre-exposure and post-exposure), there was a significant reduction in worm burden in 100 μg MCWE treated (C) mice, but not in 20 μg MCWE treated mice.

These data demonstrate that administration of MCWE, both prior and subsequent to infection with the schistosoma *S. mansoni*, significantly reduces worm burden.

Survival rates were determined for Group IV (pre-exposure and post-exposure) mice after cercarial challenge. At 16 weeks post-infection, the survival rates were 55% for Group IV-A mice (PBS), 80% for Group IV-B mice (20 μg MCWE) and 85% for Group IV-C mice (100 μg MCWE). These data demonstrate that MCWE has a significant effect on the survival of *S. mansoni* infected mice and that this effect is dose-dependent.

These data show that MCWE is effective as a therapeutic agent for treating the schistosoma *S. mansoni*.

EXAMPLE 7

PREVENTION OF *TRICHINELLA SPIRALIS* INFECTION WITH MCWE

In this study, 28 parasite free inbred NIH female mice, weighing 20–25 grams were divided into four groups. Group FCA received 0.1 ml of Freund's complete adjuvant (Sigma Chemical Co. St. Louis, Mo.) in 0.1 ml of phosphate buffered saline (PBS), pH 7.2, intrapertioneally. Group Con A received 20 μg Conconavalin A (Sigma Chemical Co. St. Louis, Mo.) intrapertioneally. Group MCWE received 100 μg of MCWE (Example II) intrapertioneally. Group Control received 0.1 ml of PBS intrapertioneally. Seven days later, each animal was orally infected with 300 infective larvae of *T. spiralis*. Forty-two days later, the animals were sacrificed and the number of larvae per gram of muscle tissue was determined. Statistical analyses were done using an ANOVA Table 3 shows the number of larvae per gram of muscle tissue in Group FCA, Group Con A, Group MCWE and Group Control 42 days after infection with *T. spiralis*.

TABLE 3

LARVAE PER GRAM OF MUSCLE

| Group | Range | Mean no. of worms ± SD | % Reduction vs. control | p value |
|---|---|---|---|---|
| FCA | 42–79 | 59.8 ± 13.1 | 15.5 | >0.05 |
| Con A | 8–28 | 17 ± 8.5 | 76 | <0.001 |
| MCWE | 0–16 | 3.3 ± 6.2 | 95.3 | <0.001 |
| Control (PBS) | 54–86 | 71 ± 11.5 | — | — |

These data show a significant reduction in larvae per gram of muscle tissue in both Group Con A and Group MCWE mice as compared to Group Control mice. There was no significant reduction in larvae per gram of muscle tissue between Group Control and Group FCA mice.

These data show that MCWE is effective as a therapeutic agent in preventing infection with the trichinella *T. spiralis*.

EXAMPLE 8

PREPARATION OF *RHODOCOCCUS EQUI* CELL WALL EXTRACT (RCWE)

*R. equii,* a coryneform organism previously designated as *Corynebacterium equi,* cell wall extract is prepared as in Example 1.

EXAMPLE 9

MMUNOSTIMULATORY PROPERTIES OF *RHODOCOCCUS EQUI* CELL WALL EXTRACT (RCWE)

Thirty-two CD1 outbred mice were injected intraperitoneally with 200 µg of RCWE in 0.5 ml of 2% oil in normal saline emulsion (RCWE mice). Sixteen CD1 outbred mice were injected intraperitoneally with 0.5 ml of normal saline (saline control mice) and 8 CD1 mice were maintained as environmental controls (environmental control mice). After 72 hours, 16 RCWE mice and 8 saline control mice were challenged with $5XLD_{50}$ of *Pasteurella multocida* and 16 RCWE mice and 8 saline control mice were challenged with $20XLD_{50}$ of encephalomyocarditis (EMC) virus. At 14 days post-challenge, 10/32 RCWE mice, 0/16 saline control mice and 8/8 environmental control mice survived.

These data demonstrate that RCWE is a nonspecific immunostimulant.

EXAMPLE 10

STIMULATION OF NITRIC OXIDE PRODUCTION BY RCWE AND BY MCWE

Murine macrophage cell line RAW 264.7 cells were plated in 24 well tissue plates. When the cells formed a confluent monolayer, media was removed from the wells and replaced with 1 ml of fresh media containing from 5–80 µg of RCW or 5–80 µg of MCWE. After 24 hours incubation at 37° C. in an atmosphere containing 5% $CO_2$, nitric oxide (NO) production was determined using the calorimetric reaction of Griess (Griess, P. Demerkungen zu der Abhandlung der HH. Wesdlsky und Benedikt. UEBER EINIGE AZOVERDINDUNGEN. Chem. Ber. 12: 426–428, 1987).

TABLE 4

Mean Nitric Oxide (NO) Production (nMol/$10^6$ cells/24 h)

| SAMPLE | 5 µg | 10 µg | 20 µg | 40 µg | 80 µg |
|---|---|---|---|---|---|
| RCWE[1] | 0.0336 | 0.0986 | 0.1926 | 0.2540 | 0.2773 |
| MCWE[2] | 0.1650 | 0.2124 | 0.2600 | 0.2910 | 0.3107 |

[1]Mean of all samples for RCWE
[2]Mean of all samples for MCWE

The data in Table 4 demonstrate that the nonspecific immunostimulant RCWE has nonspecific immunostimulatory properties similar to those of the nonspecific immunostimulant MCWE in promoting the generation of NO by RAW 264.7 cells.

It should be understood, of course, that the foregoing relates only to preferred embodiments of the present invention and that numerous modifications or alterations may be made therein without departing from the spirit and the scope of the invention as set forth in the appended claims.

We claim:

1. A method for treating a disease in an animal caused by a parasite selected from the group consisting of a Babesia, a Schistosoma and a Trypanosoma, comprising administering to the animal an amount of a *Mycobacterium phlei* cell wall extract effective to treat the parasitic disease in the animal.

2. A method for eliminating a disease in an animal caused by a parasite selected from the group consisting of a Babesia, a Schistosoma and a Trypanosoma, comprising administering to the animal an amount of a *Mycobacterium phlei* cell wall extract effective to eliminate the parasitic disease in the animal.

3. The method of claim 1, wherein the parasite is a Schistosoma.

4. The method of claim 1, wherein the parasite is a Trypanosoma.

5. The method of claim 2, wherein the parasite is a Schistosoma.

6. The method of claim 2, wherein the parasite is a Trypanosoma.

7. The method of claim 1, wherein the parasite is a Babesia.

8. The method of claim 2, wherein the parasite is a Babesia.

* * * * *

UNITED STATES PATENT AND TRADEMARK OFFICE
CERTIFICATE OF CORRECTION

PATENT NO. : 6,139,844
DATED : October 31, 2000
INVENTOR(S) : Alkemade et al.

It is certified that error appears in the above-identified patent and that said Letters Patent is hereby corrected as shown below:

Title page,
Title, "PARASITIC" should read -- PROTOZOAL --.

Abstract,
Line 1, delete "or parasitic".
Line 4, delete "or parasitic".

Column 1,
Line 2, "PARASITIC" should read -- PROTOZOAL --.

Claims,
Column 14, claim 1,
Line 33, "parasite" should read -- protozoa --.
Line 36, "parasitic" should read -- protozoal --.

Column 14, claim 2,
Line 39, "parasite" should read -- protozoa --.
Line 42, "parasitic" should read -- protozoal --.

Column 14, claim 3,
Line 45, "parasite" should read -- protozoa --.

Column 14, claim 4,
Line 47, "parasite" should read -- protozoa --.

UNITED STATES PATENT AND TRADEMARK OFFICE
CERTIFICATE OF CORRECTION

PATENT NO. : 6,139,844
DATED : October 31, 2000
INVENTOR(S) : Alkemade et al.

It is certified that error appears in the above-identified patent and that said Letters Patent is hereby corrected as shown below:

Column 14, claim 5,
Line 49, "parasite" should read -- protozoa --.

Column 14, claim 6,
Line 51, "parasite" should read -- protozoa --.

Column 14, claim 7,
Line 53, "parasite" should read -- protozoa --.

Column 14, claim 8,
Line 55, "parasite" should read -- protozoa --.

Signed and Sealed this

Sixth Day of November, 2001

*Attest:*

NICHOLAS P. GODICI
*Attesting Officer*  Acting Director of the United States Patent and Trademark Office